(12) United States Patent
Schipke et al.

(10) Patent No.: US 7,796,276 B2
(45) Date of Patent: Sep. 14, 2010

(54) APPARATUS AND METHOD FOR EXAMINING A CURVED SURFACE

(75) Inventors: Joerg Schipke, Malsch (DE); Matthias Westenhoefer, Offenburg (DE)

(73) Assignee: ISRA Vision AG, Darmstadt (DE)

( * ) Notice: Subject to any disclaimer, the term of this patent is extended or adjusted under 35 U.S.C. 154(b) by 279 days.

(21) Appl. No.: 11/909,141

(22) PCT Filed: Mar. 20, 2006

(86) PCT No.: PCT/EP2006/002519

§ 371 (c)(1),
(2), (4) Date: Sep. 19, 2007

(87) PCT Pub. No.: WO2006/100010

PCT Pub. Date: Sep. 28, 2006

(65) Prior Publication Data

US 2008/0192261 A1 Aug. 14, 2008

(30) Foreign Application Priority Data

Mar. 24, 2005 (DE) .................. 10 2005 014 415

(51) Int. Cl.
*G01B 11/24* (2006.01)

(52) U.S. Cl. ...................... 356/601; 356/612

(58) Field of Classification Search ............... 356/601, 356/609, 611, 612, 237.1–237.5; 348/92, 348/128, 131, 132, 125
See application file for complete search history.

(56) References Cited

U.S. PATENT DOCUMENTS

| 4,984,886 A | 1/1991 | Yoshida |
| 5,825,495 A * | 10/1998 | Huber .................. 356/600 |

FOREIGN PATENT DOCUMENTS

| DE | 35 00 332 | 8/1985 |
| DE | 198 54 942 | 6/2007 |
| WO | 00/00814 | 1/2000 |

OTHER PUBLICATIONS

Arasa, J., et al: "Concave Reflective Surfaces . . . " Emerging Technologies and Factory Automation 1999 Proceedings, 7-th IEEE International Conference in Barcelona, Spain Oct. 18-21, 1999,and Piscataway, NJ, USA on Oct. 18, 1999, pp. 1147-1154. (in English).

* cited by examiner

*Primary Examiner*—Gregory J Toatley, Jr.
*Assistant Examiner*—Tri T Ton
(74) *Attorney, Agent, or Firm*—Michael J. Striker

(57) ABSTRACT

An apparatus and a method for examining a curved surface (5), having a camera (2) and an objective (3) and a lamp (4), is described. The camera (2) can be aimed at the inside of the curved surface (5), and the lamp (4) can be located such that light (7) emitted by the lamp (4) is reflected from the inside of the curved surface (5) into the camera (2). To attain high contrast with a simple arrangement, the lamp (4) is located in the beam path of the objective (3) of the camera (2).

7 Claims, 1 Drawing Sheet

APPARATUS AND METHOD FOR EXAMINING A CURVED SURFACE

BACKGROUND OF THE INVENTION

The invention relates to an apparatus and a method for examining a reflective surface, in particular one that is curved inward, with a camera having an objective and with a lamp; the camera can be aimed at the inside of the curved surface, and the lamp can be located such that light emitted by the lamp is reflected from the inside of the curved surface into the camera.

By lighting and taking pictures of surfaces, it is possible to recognize structures on the surfaces by means of conventional image evaluation methods connected to the optical cameras. If weak structures on reflective curved surfaces are to be made visible, the lighting and optical arrangements employed until now, such as lighting in the form of a bright and/or dark field that shines either diffusely or in an aimed way, do not lead to sufficient contrast for simple image evaluation. Other examination methods, such as white-light interferometry or a confocal measuring system, conversely, are complicated, expensive, and too slow in their examination speed.

It is therefore the object of the invention to propose a possible way of examining curved surfaces, which with a structurally simple construction achieves adequate contrast of the surface to be examined.

SUMMARY OF THE INVENTION

This object is attained by an apparatus having the characteristics of claim 1 and a method having the characteristics of claim 7. In the apparatus of the invention, it is provided in particular that the lamp is located in the beam path of the objective of the camera. By locating the lamp in the beam path of the camera objective, it can be attained that the lamp shines at the curved surface with a wide projection angle and illuminates it uniformly. The curved surface assures that the light at every point of the curvature is focused into the camera and reflected into the camera. Surface structures are lent sufficient contrast by the uniform lighting because of the focusing of the light and can be evaluated easily with conventional methods of image processing. Because of the high contrast attained, a comparatively short exposure time for the images can also be employed, so that even moving surfaces can be examined without having to interrupt the motion, for instance during a production.

In one embodiment of the invention, the lamp may comprise a lighting means and optics that focus the light generated by the lighting means into the beam path of the objective. To that end, the optics can have lenses for focusing the light and can have a mirror, which in particular is semitransparent, and which is located in the beam path of the objective of the camera. The optical system is adjusted such that the light is focused essentially in pinpoint form on the mirror, so that it shines on the curved surface over a wide projection angle.

However, such optics have many individual components, which leads to comparatively large dimensions of the apparatus. Moreover, the individual components require complicated calibration. A more easily manipulated apparatus can be achieved by providing that the lamp is an in particular pinpoint light source. The term pinpoint light source should be understood to mean a small lighting means in terms of its dimensions, compared to the camera objective and to the surface to be examined, such as an LED light. The pinpoint or small light source emits light with a wide projection angle at the inside of the curved surface, and the light is focused there and reflected into the camera without requiring that complicated optics be provided. The examined surface of the object is thus illuminated homogeneously. Areas of the surface that do not reflect the light into the objective, such as structures like cracks, dents, or similar irregularities, then appear markedly darker. This creates sufficient contrast that is easy to evaluate, making it possible for surface structures to be recognized even with simple, conventional image evaluation.

According to the invention, the lamp may be located centrally, in particular on the optical axis of the camera, so as to attain lighting of the curved surface that is as uniform as possible with regard to the camera image.

In a preferred embodiment of the invention, the lamp is not located in the focus of the camera. For recognition of the surface structure, the camera is adjusted focally (image sharpness) in such a way that the curved surface is reproduced sharply in the camera. The lamp, in particular the pinpoint light source, is then located outside the image sharpness of the camera, so that the camera looks around the light means. Thus the lighting means is not visible in the camera image, and the object surface is reproduced without interfering contours. A particular advantage of the invention resides in this arrangement, especially if the pinpoint light source is small in comparison to the diameter of the camera objective.

It has been found that the lamp or pinpoint light source is especially inconspicuous in the camera image if the spacing of the lamp from the curved surface in operation of the apparatus is greater than the spacing of the lamp from the objective of the camera. In particular, the lamp can be brought as close as possible to the objective; for instance, it can even be fixed on the objective itself. It can furthermore be advantageous if the spacing of the light source from the camera is adjustable, for instance even during operation.

The curved surface preferably has a shape similar to a concave mirror. If the shape is like a concave mirror or at least cylindrical, the focusing of the light can be achieved especially well. The apparatus is therefore especially well suited for examining metal surfaces, for instance of metal packages such as cans, whose curved side wall or bottom is to be examined.

The stated object is also attained by methods for examining a reflective surface, in particular one that is concave, with a camera and an objective in which the curved surface is illuminated with a light, and the light emitted by the lamp is reflected from the inside of the curved surface into the camera. The lamp, embodied in particular as a pinpoint light source of only slight extent, is located in the beam path of the objective. In this arrangement, by means of the method of the invention, the reflection from the curved surface of the objective is utilized similarly to the way it is done in a concave mirror for focusing the beams of light. As a result, uniform illumination of the curved surface and high contrast of surface structures on the curved surface are attained, since the surface structures scatter the reflected light from the camera and appear dark on the otherwise bright surface. The method of the invention can be performed in particular with the apparatus described above.

Preferably, the camera focus is set not to the lamp but to the curved surface, so that the surface structures can be recognized precisely. It is advantageous for the lamp to be located according to the invention outside the area of great depth of field of the objective, in order to cause the camera to look around the lamp or light source and so that no interfering contours of the lamp will be detectable in the camera image.

To that end, the lamp, for instance upon startup, can be moved toward the objective of the camera until such time as the lamp is no longer visible in the camera image, and/or until the lamp is fixed on the objective.

According to the invention, the method can be employed especially well for contrasting surface structures on curved metal surfaces, in particular of metal packages such as cans.

By the location according to the invention of a small light source or a small lighting means in the beam path of the camera objective, especially good illumination and contrast can be achieved by focusing the existing light, without the light source, given its location outside the focus of the camera, being visible in the camera image.

Further characteristics, advantages and possible uses of the present invention will become apparent as well from the ensuing description of an exemplary embodiment and from the drawing. All the characteristics described and/or shown in the drawing, on their own or in arbitrary combination, form the subject of the present invention, regardless of how they are summarized in the claims and regardless of the claims dependencies.

DETAILED DESCRIPTION OF THE INVENTION

Figure 1:
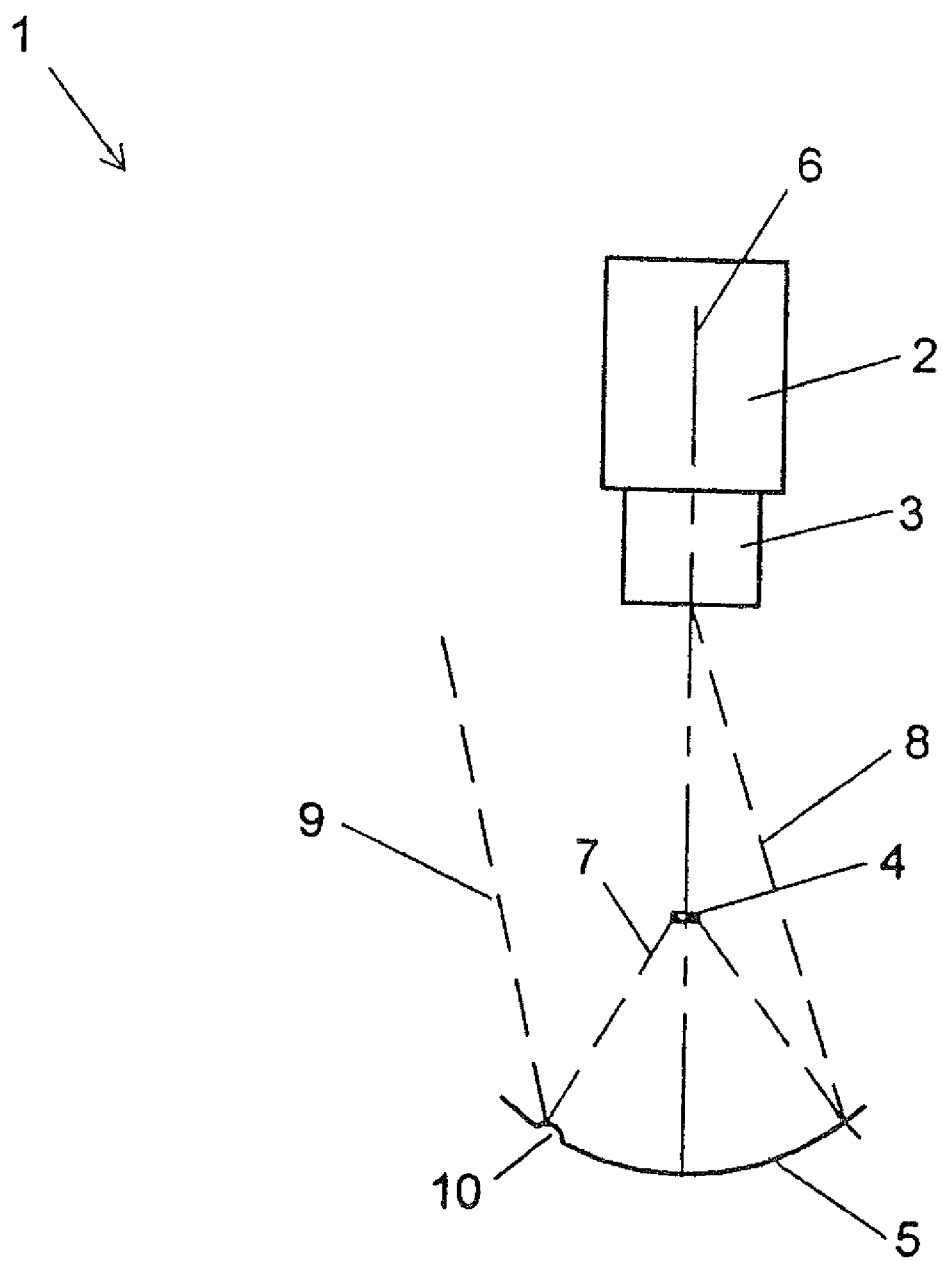
FIG. 1 is a schematic diagram depicting one embodiment of an Apparatus For Examining A Curved Surface.

The sole drawing, FIG. 1, shows an apparatus 1 according to the invention for examining an inwardly curved surface 5 of an object. The object has a reflective surface and may for instance be of metal. In particular, the apparatus 1 can be used to examine metal packages, such as cans. However, the apparatus is not limited to that use and can be employed in general for examining curved, reflective surfaces.

The apparatus 1 has a camera 2 with an objective 3 that is aimed and focused at the inwardly curved surface 5 to be examined. In a housing, not shown, of the apparatus 1, there is also a lamp 4, embodied as a pinpoint light source, located such that the light 7 emitted by the light source 4 illuminates the inside of the curved surface 5 with a wide projection angle and is reflected in focused form because of the curvature of the surface 5.

The camera 2 is located relative to the light source 4 in such a way that the reflected light 8 from the curved surface 5 enters the camera 2 through the objective 3. As a result, the surface 5 appears bright. To achieve uniform illumination of the curved surface 5, the light source 4 is located in the beam path of the objective 3 of the camera 4 and rests with its center on the optical axis 6 of the camera 2, or of the objective 3.

Since the light source 4 is located outside the focus or image sharpness range of the camera 2 and is small in its dimensions in comparison to the diameter of the objective 3, the camera 2 looks around the light source 4, which thus does not appear as an interfering contour in the camera image. The entire curved surface 5 can therefore be reliably examined, examined, yet the light source 4, located in the beam path of the objective 3, is not a hindrance. In this arrangement, highly uniform illumination of the curved surface 5 can be achieved in a very compact arrangement if for examining the surface it is located with its center point in or in the vicinity of the optical axis 6 of the camera 2, so as to attain an overall symmetrical arrangement.

For adjusting the emitted and reflected light 7, 8, the camera 2 and the light source 4 in the apparatus 1 can be adjusted, particularly along the optical axis 6, both relative to one another and jointly relative to the curved surface 5, by suitable adjusting means.

When the apparatus 1 is used for examining the curved surface 5, the emitted light beams 7 from the light source 4 are reflected at the unhindered surface 5 and are detected by the camera 2 in the form of reflected light beams 8, which cause the entire surface 5 to appear bright.

When a surface structure 10, such as a crack, dent, bump, or the like, is present on the surface 5, the emitted beam of light 7 is not reflected into the camera 2 but instead scattered diffusely as scattered light 9. The area of the surface structure 10 therefore looks dark in the image made by the camera 2. Because of the good focusing of the light in the surface 5, which causes the unstructured surface 5 to appear especially bright, high contrast in the area of the surface structure 10 is created by the invention. The image made by the camera 2 can therefore be evaluated with conventional image evaluation, which is part of the apparatus 1 and is connected to the camera 2.

Because of the location according to the invention of the light source 4 in the beam path of the objective 3, the reflected surface curvature is optimally utilized for focusing the existing light and increasing the contrast, yet the light source 4, located outside the focus of the camera 2, is not visible in an interfering way in the camera image. The invention therefore enables a contrasting method for examining curved surfaces that can be performed by a simply constructed apparatus 1.

LIST OF REFERENCE NUMERALS

1 Apparatus for examining a curved surface
2 Camera
3 Objective
4 Lamp, light source
5 Curved surface
6 Optical axis
7 Emitted light
8 Scattered light
9 Reflected light
10 Surface structure

What is claimed is:

1. An apparatus for examining a curved surface having a camera with an objective and a lamp, the camera being capable of being aimed at the inside of the curved surface, and the lamp being capable of being located such that light emitted by the lamp is reflected from the inside of the curved surface into the camera, wherein the lamp is located in the beam path of the objective at a position outside of the focus of the camera, wherein the lamp is an in particular pinpoint light source, wherein the lamp is located on the optical axis of the camera.

2. The apparatus as defined by claim 1, wherein the spacing of the lamp from the curved surface in operation of the apparatus is greater than the spacing of the lamp from the objective of the camera.

3. The apparatus as defined by claim 1, wherein the curved surface has a shape similar to a concave mirror.

4. A method for examining a curved surface, having a camera with an objective, in which the curved surface is lighted with a lamp, and the light emitted by the lamp is reflected from the inside of the curved surface into the camera, wherein the lamp, embodied in particular as a pinpoint light source of only slight extent, is located in the beam path of the objective at a position outside of the focus of the camera and on an optical axis of the camera.

5. The method as defined by claim 4, wherein the focus of the camera is not set to the lamp.

6. The method as defined by claim 4, wherein the lamp is moved toward the objective of the camera until one of such time as the lamp is no longer visible in the camera image, and such time as the lamp is fixed on the objective.

7. The method as defined by claim 4, wherein the method is employed for contrasting surface structures on curved metal surfaces, in particular metal packages such as cans.

* * * * *